(12) United States Patent
Bao et al.

(10) Patent No.: US 11,639,884 B2
(45) Date of Patent: May 2, 2023

(54) SHEAR CONTROL INSTRUMENT UNDER THREE-DIMENSIONAL SPACE CONDITION AND CONTROL METHOD OF SHEAR CONTROL INSTRUMENT

(71) Applicant: SHENZHEN UNIVERSITY, Guangdong (CN)

(72) Inventors: Xiaohua Bao, Guangdong (CN); Jun Shen, Guangdong (CN); Xiangsheng Chen, Guangdong (CN); Hongzhi Cui, Guangdong (CN); Yaohong Zhu, Guangdong (CN); Jinqing Jia, Guangdong (CN)

(73) Assignee: SHENZHEN UNIVERSITY, Guangdong (CN)

( * ) Notice: Subject to any disclaimer, the term of this patent is extended or adjusted under 35 U.S.C. 154(b) by 0 days.

(21) Appl. No.: 17/821,526

(22) Filed: Aug. 23, 2022

(65) Prior Publication Data
US 2023/0063597 A1 Mar. 2, 2023

(30) Foreign Application Priority Data

Aug. 26, 2021 (CN) .......................... 202110992271.X

(51) Int. Cl.
*G01N 3/24* (2006.01)
*G01N 33/24* (2006.01)

(52) U.S. Cl.
CPC .............. *G01N 3/24* (2013.01); *G01N 33/24* (2013.01); *G01N 2203/0025* (2013.01); *G01N 2203/0676* (2013.01); *G01N 2203/0682* (2013.01)

(58) Field of Classification Search
CPC ..................... G01N 33/24; G01N 3/24; G01N 2203/0025; G01N 2203/0676; G01N 2203/068; G01N 29/022; G01N 35/00871; G01N 21/8851; G01N 21/39; G05B 23/254; G05B 23/0243; G05B 23/0283; G06N 3/088; G06N 20/00; G01B 11/002;
(Continued)

(56) References Cited

U.S. PATENT DOCUMENTS

| 10,690,649 | B2 * | 6/2020 | Zhang | ................... | G01N 17/00 |
| 2012/0060588 | A1 * | 3/2012 | Ng | ......................... | G01N 33/24 |
| | | | | | 73/866 |
| 2015/0377853 | A1 * | 12/2015 | Feng | ...................... | G01N 15/08 |
| | | | | | 73/863 |

FOREIGN PATENT DOCUMENTS

CN 103969107 A 8/2014
CN 110987638 A * 4/2020

OTHER PUBLICATIONS

First Office Action from CN 202110992271 .X, dated Jan. 4, 2022.
(Continued)

*Primary Examiner* — Brandi N Hopkins
(74) *Attorney, Agent, or Firm* — Mark T. Vogelbacker; Eckert Seamans Cherin & Mellott, LLC

(57) ABSTRACT

A shear control instrument under a three-dimensional space condition and a control method of the shear control instrument can include a loading system, a transposition system and a control monitoring system. The loading system is used for loading a soil body sample. The transposition system is connected with the loading system in an anchoring manner and is used for adjusting the direction of the loading system. The control monitoring system is connected with the transposition system in an anchoring manner and is used for controlling the transposition system and monitoring test data.

7 Claims, 5 Drawing Sheets

(58) Field of Classification Search
CPC ...... G01L 5/0052; G10H 5/007; G06K 9/623; G06K 9/6247; G01P 5/245; G01R 33/56358
See application file for complete search history.

(56) References Cited

OTHER PUBLICATIONS

The Second Office Action from CN 202110992271 .X, dated Feb. 14, 2022.
Notification to Grant Patent Rights for Invention from CN 202110992271 .X, dated Mar. 23, 2022.

* cited by examiner

United States Patent US 11,639,884 B2

SHEAR CONTROL INSTRUMENT UNDER THREE-DIMENSIONAL SPACE CONDITION AND CONTROL METHOD OF SHEAR CONTROL INSTRUMENT

CROSS REFERENCE TO RELATED APPLICATION

This patent application claims the benefit and priority of Chinese Patent Application No. 202110992271.X, filed on Aug. 26, 2021, the disclosure of which is incorporated by reference herein in its entirety as part of the present application.

TECHNICAL FIELD

The present disclosure relates to the application field of shear control instruments, in particular to a shear control instrument under a three-dimensional space condition and a control method of the shear control instrument.

BACKGROUND ART

In the field of geotechnical engineering, roadbed backfilling, foundation pit excavation, tunnel excavation, traffic vibration, earthquakes and the like all meet the situation that soil is in stress-induced anisotropy. The complex stress states are external conditions generated by anisotropy, and the assumption of actual solutions and the actual soil situation lead to large errors. Therefore, the risk of causing geotechnical engineering accidents is caused, and the mechanism research needs to be broken through.

But for a long time, the research of soil mechanics is based on an average theory and a homogenization theory, and a soil body is assumed to be an anisotropic material for analysis. However, the soil body is actually formed by combining a plurality of soil particles with different sizes according to a certain sequence, physical mechanics differences exist in all directions, and the anisotropic characteristics, including material anisotropy and stress anisotropy, are presented.

In an existing soil mechanics test instrument, two kinds of anisotropy are mainly considered separately. For example, stress anisotropy is considered by adopting a true triaxial instrument, and anisotropy of materials is considered by adopting a hollow cylindrical torsional shear instrument. The two test instruments and methods cannot comprehensively consider the materials and the stress for testing. However, more and more research suggests that there is some close association between material anisotropy and stress principal axis rotation.

Therefore, the prior art has yet to be improved.

SUMMARY

Aiming at the defects in the prior art, the technical problem to be solved by the present disclosure is to provide a shear control instrument under a three-dimensional space condition and a control method of the shear control instrument so as to solve the technical problem that an existing geomechanical test instrument cannot perform combined tests on materials and stresses.

The technical scheme adopted for solving the technical problem of the present disclosure is as follows.

In the first aspect, the present disclosure provides a shear control instrument under a three-dimensional space condition, comprising a loading system, a transposition system and a control monitoring system, wherein the loading system is used for loading a soil body sample; the transposition system is connected with the loading system in an anchoring manner and is used for adjusting the direction of the loading system; and the control monitoring system is connected with the transposition system in an anchoring manner and is used for controlling the transposition system and monitoring test data.

In an implementation method, the loading system comprises loading mechanical arms, loading plates and a main body loading steel frame;

one end of each of the loading mechanical arms is rotatably connected with the loading plate, and the other ends of the loading mechanical arms are rotatably connected with the control monitoring system; and the loading mechanical arms and the loading plates are fixedly connected with the main body loading steel frame through the transposition system.

In an implementation method, an inner spherical groove is formed in one side of the loading plate, a spherical body is arranged at one end of the loading mechanical arm, and the dimensions of the inner spherical groove are matched with those of the spherical body; and the spherical body is embedded in the inner spherical groove, and the loading mechanical arm is rotatably connected with the loading plate through the spherical body.

In an implementation method, the main body loading steel frame comprises a rectangular test box and an upper cladding sheet; and the rectangular test box is detachably connected with the upper cladding sheet.

In an implementation method, the transposition system comprises telescopic mechanical rods for telescopically controlling the directions of the loading plates and sliding plates used for the telescopic mechanical rods to slide;

the sliding plate is fixedly connected with the rectangular test box through bolts; the sliding plate is fixedly connected with the upper cladding sheet through bolts; and the telescopic mechanical rod is slidably connected with the sliding plate.

In an implementation method, the telescopic mechanical rod is arranged between the sliding plate and the loading plate, one end of the telescopic mechanical rod is slidably connected with the sliding plate, and the other end of the telescopic mechanical rod is rotatably connected with the loading plate.

In an implementation method, the control monitoring system comprises a control device for adjusting the telescopic mechanical rods and the loading mechanical arms and monitoring devices for monitoring strain data, related to anisotropy of an inclined consolidation material, of loading shear in the three-dimensional space;

the control device and the monitoring devices are respectively connected with a computer system;

the monitoring devices comprise optical fiber sensors and/or a CCD camera; the optical fiber sensor is arranged on the inner side of the sliding plate, and is fixedly connected with the sliding plate; the CCD camera is arranged on the main body loading steel frame, and is fixedly connected with the main body loading steel frame; and the optical fiber sensors and the CCD camera are mutually independent monitoring devices.

In the second aspect, the present disclosure further provides a control method of a shear control instrument under a three-dimensional space condition, comprising the following steps:

placing the soil body sample on the loading plates and adjusting the three-dimensional space angle of the soil body sample according to loading parameters so as to realize the test consolidation process on different deposition inclined planes;

reducing the telescopic mechanical rods and controlling the angles of the loading mechanical arms and the telescopic amounts of the telescopic mechanical rods through the control device so as to load the soil body sample;

recoding variables in the loading process, and calculating the stress and strain data loaded in all directions according to the variables; and forming first text data according to the strain data and temperature data collected by the optical fiber sensors, forming second text data according to images shot by the CCD camera, and drawing dynamic test images of the soil body sample in combination with the first text data, the second text data, soil body sample data and the loading parameters.

In an implementation method, the step of placing the soil body sample on the loading plates and adjusting the three-dimensional spatial angle of the soil body sample comprises the following substeps:

placing the soil body sample on the loading plates inside the main body loading steel frame;

adjusting the control device, adjusting the telescopic mechanical rods, and adjusting the loading plates to be in complete contact with the soil body sample and to be fixed; and obtaining the loading parameters, and adjusting the three-dimensional space angle of the soil body sample according to the loading parameters.

In an implementation method, the step of recording variables in the loading process, and calculating the stress and strain data loaded in all directions according to the variables comprises the following substeps:

obtaining the dimension parameters and the weight parameter of the soil body sample;

recording the angles of the loading mechanical arms, the telescopic amounts of the telescopic mechanical rods and the strain capacity of the soil body sample in the recording process; and calculating the stress and strain data loaded in all directions, and forming calculation files according to the stress and strain data so as to export or display the calculation files.

The present disclosure has the following effects by adopting the technical scheme.

The soil body sample is loaded through the loading system, and the shear stress and normal stress coordinated change of the soil body sample is controlled under the coordinated adjustment of the transposition system and the control monitoring system, so that a fixed-axis shear stress path in which different stress principle axis directions are changed and the shear stress is gradually increased can be realized. A shear test with unchangeable deviatoric stress level and continuous change of a large principal stress direction angle is carried out, so that the problem that only three principal stress magnitudes and a single direction vector can be controlled in a soil mechanics test at the present stage can be solved, and simultaneous control for directions and size in the three-dimensional space is realized.

BRIEF DESCRIPTION OF THE DRAWINGS

To describe the technical solutions in the embodiments of the present disclosure or in the prior art more clearly, the following briefly describes the attached figures required for describing the embodiments or the prior art. Apparently, the attached figures in the following description show some embodiments of the present disclosure, and a person of ordinary skill in the art may still derive other attached figures from these attached figures without creative efforts.

Reference signs: 1, main body loading steel frame; 2, sliding plate; 3, loading mechanical arm; 4, loading plate; 5, telescopic mechanical rod; 6, control device; 7, soil body sample; 21, anchoring part; 22, bolt; 31, spherical body; and 41, inner spherical groove.

The object realization, functional characteristics and advantages of the present disclosure are further described with reference to the attached figures in conjunction with the embodiments.

DETAILED DESCRIPTION OF THE EMBODIMENTS

In order to make the objectives, technical solutions and advantages of the present disclosure clearer, the present disclosure will be further described hereinbelow with reference to the attached figures and embodiments thereof. It shall be understood that, the embodiments described herein are only intended to illustrate but not to limit the present disclosure.

EMBODIMENTS

Please refer to FIG. 1 to FIG. 7.

Figure 1:
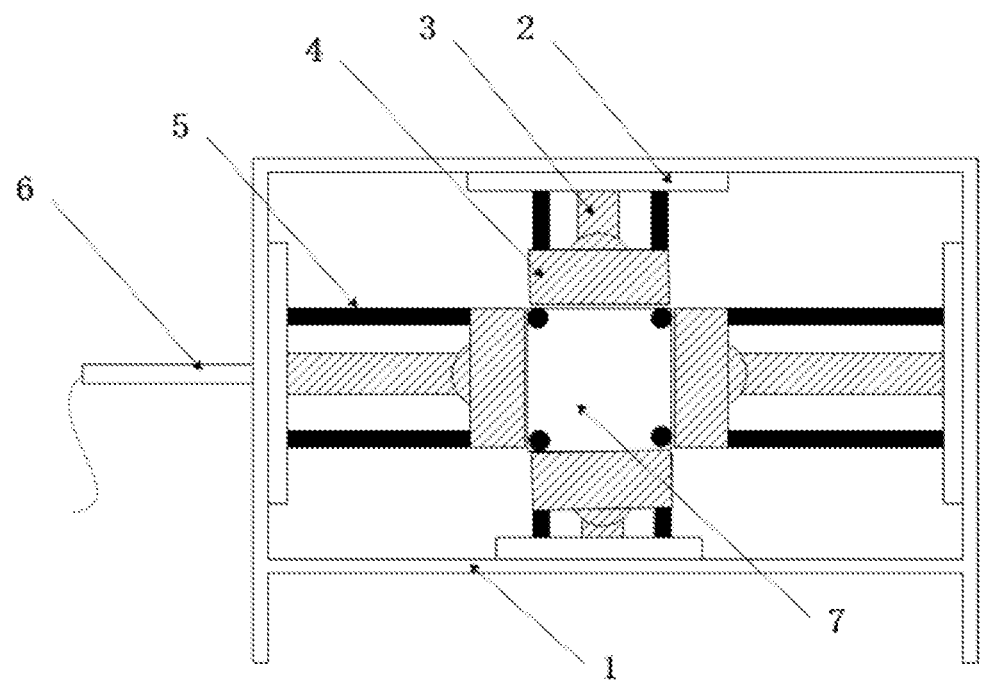
FIG. 1 is a structural schematic diagram of a shear control instrument (in an installation state) under a three-dimensional space condition in an implementation method of the present disclosure.
Figure 3:
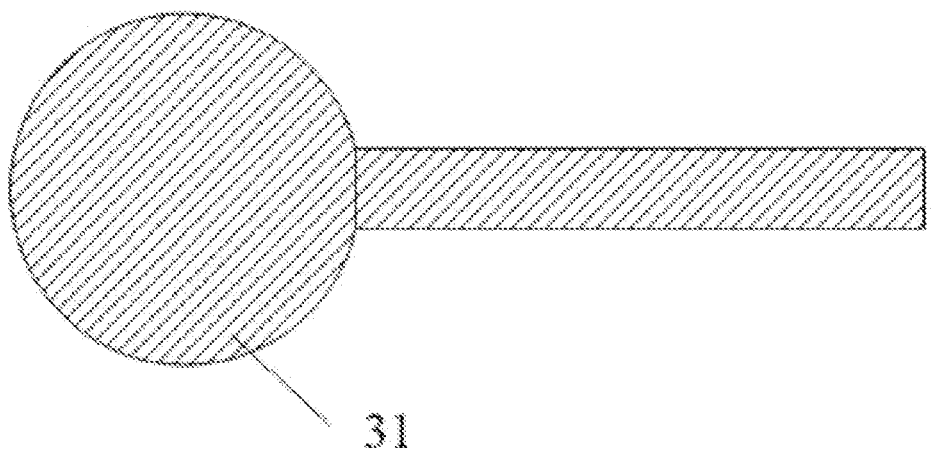
FIG. 3 is a structural schematic diagram of a loading mechanical arm in an implementation method of the present disclosure.

As shown in FIG. 1 and FIG. 3, the embodiment provides a shear control instrument under a three-dimensional space condition, comprising a loading system, a transposition system and a control monitoring system, wherein the loading system is used for loading a soil body sample 7 (namely a cubic sample); the transposition system is connected with the loading system in an anchoring manner and can be used for adjusting the direction of the loading system under the adjustment of the control monitoring system; and the control monitoring system is connected with the transposition system in an anchoring manner and can be used for controlling the transposition system and monitoring test data.

Figure 2:
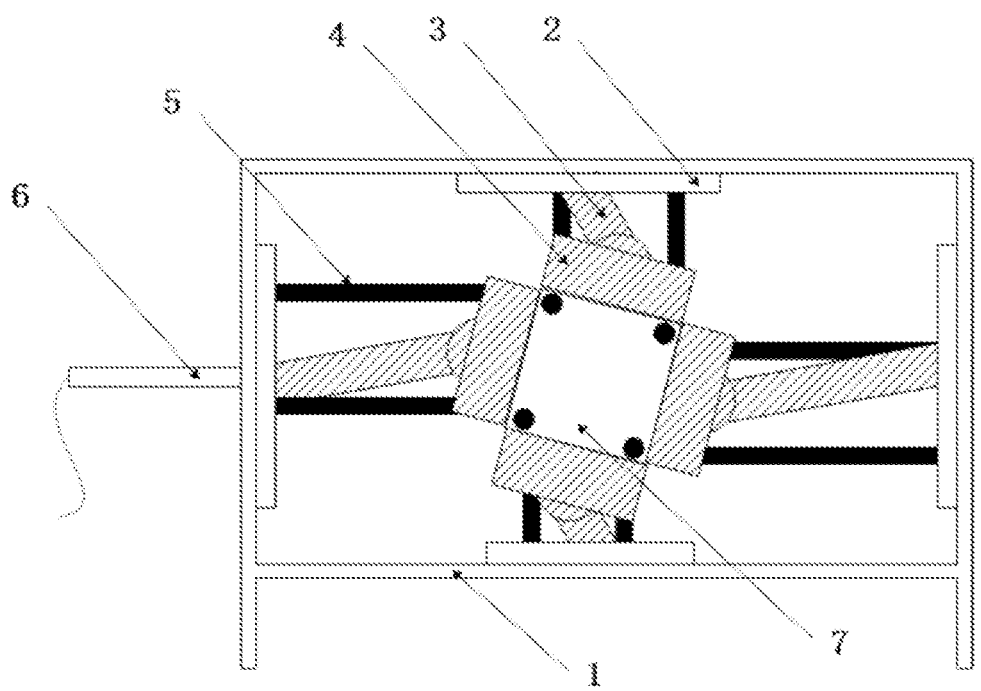
FIG. 2 is a structural schematic diagram of a shear control instrument (in a test state) under a three-dimensional space condition in an implementation method of the present disclosure.

As shown in FIG. 2, according to the embodiment, the loading direction and force of the loading system can be adjusted through the control monitoring system and the transposition system, so that the shear stress and normal stress coordinated change of the soil body sample is controlled, and a fixed-axis shear stress path in which different stress principle axis directions are changed and the shear stress is gradually increased can be realized. A shear test with unchangeable deviatoric stress level and continuous change of a large principal stress direction angle is carried out, so that the problem that only three principal stress magnitudes and a single direction vector can be controlled in a soil mechanics test at the present stage can be solved, and simultaneous control for directions and size in the three-dimensional space is realized.

Specifically, as shown in FIG. 1 and FIG. 2, the loading system comprises loading mechanical arms 3, loading plates 4 and a main body loading steel frame 1; one end of each of the loading mechanical arms 3 is rotatably connected with the loading plate 4, and the other ends of the loading mechanical arms are rotatably connected with the control monitoring system; and the loading mechanical arms 3 and the loading plates 4 are fixedly connected with the main body loading steel frame 1 through the transposition system.

Figure 4:
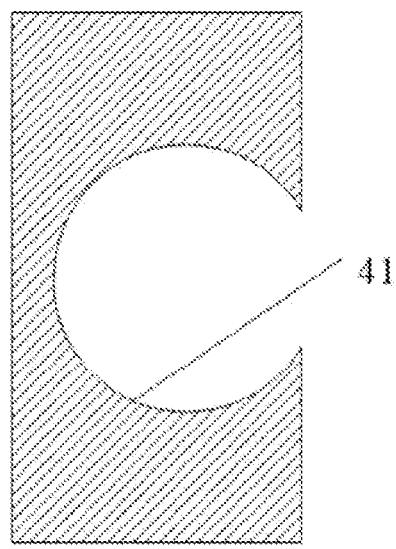
FIG. 4 is a structural schematic diagram of a loading plate in an implementation method of the present disclosure.

Further, as shown in FIG. 3 and FIG. 4, an inner spherical groove 41 is formed in one side of the loading plate 4, a spherical body 31 is arranged at one end of the loading mechanical arm 3, and the dimensions of the inner spherical groove 41 are matched with those of the spherical body 31; and the spherical body 31 is embedded in the inner spherical groove 41, and the loading mechanical arm 3 is rotatably connected with the loading plate 4 through the spherical body 31.

In the embodiment, the loading system may comprise six loading mechanical arms 3, six loading plates 4 and a main body loading steel frame 1; the six loading mechanical arms 3 are respectively arranged on the six inner side faces of the main body loading steel frame 1, and the six loading plates 4 and the loading mechanical arms 3 are arranged in a one-to-one correspondence manner; the main body loading steel frame 1 may comprise a rectangular test box and an upper cladding sheet, and the rectangular test box is detachably connected with the upper cladding sheet; and sixteen bolt holes are formed in the five inner side faces of the rectangular test box so that the sliding plates 2 of the transposition system are conveniently installed.

The end, connected with the loading plate 4, of the loading mechanical arm 3 can rotate at the joint, so that the loading direction of the loading plate 4 is adjusted. The magnitude of the loading force of the loading plate 4 can be adjusted through the control monitoring system at the end, connected with the control monitoring system, of the loading mechanical arm 3. One end of the loading plate 4 is connected with the loading mechanical arm 3, and the other end of the loading plate 4 is connected with the soil body sample 7.

Figure 5:
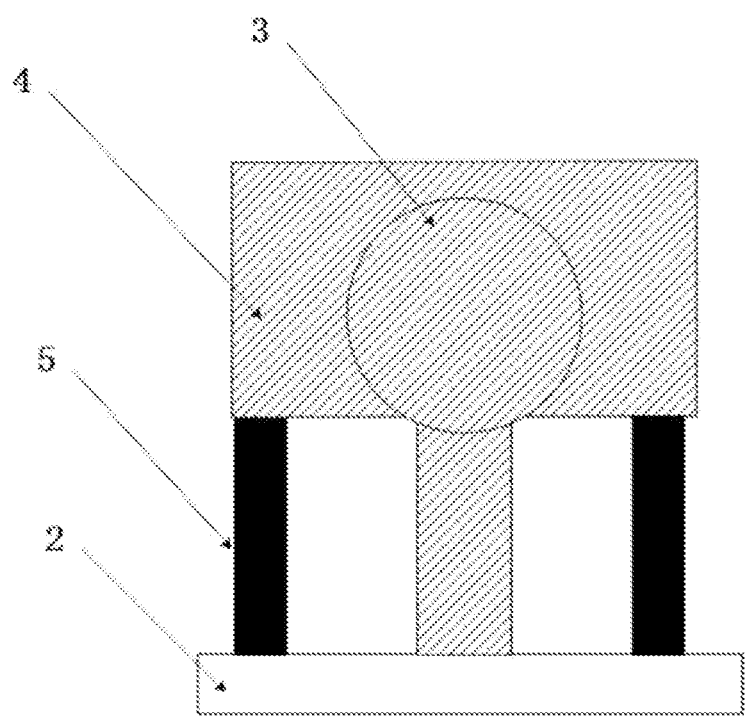
FIG. 5 is an assembly schematic diagram (at a first perspective) of a loading system and a transposition system in an implementation method of the present disclosure.
Figure 6:
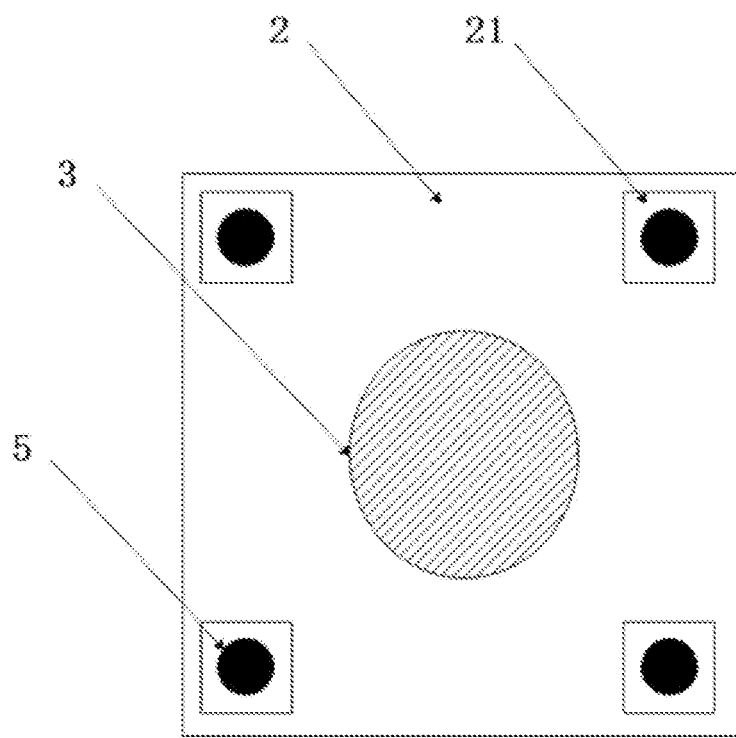
FIG. 6 is an assembly schematic diagram (at a second perspective) of a loading system and a transposition system in an implementation method of the present disclosure.

Specifically, as shown in FIG. 5 and FIG. 6, the transposition system comprises telescopic mechanical rods 5 and sliding plates 2, wherein the telescopic mechanical rods can be used for telescopically controlling the directions of the loading plates, and the sliding plates 2 are used for the telescopic mechanical rods 5 to slide. The sliding plate 2 is fixedly connected with the rectangular test box through bolts 22. The sliding plate 2 is fixedly connected with the upper cladding sheet through bolts 22. The telescopic mechanical rod 5 is slidably connected with the sliding plate 2.

Figure 7:
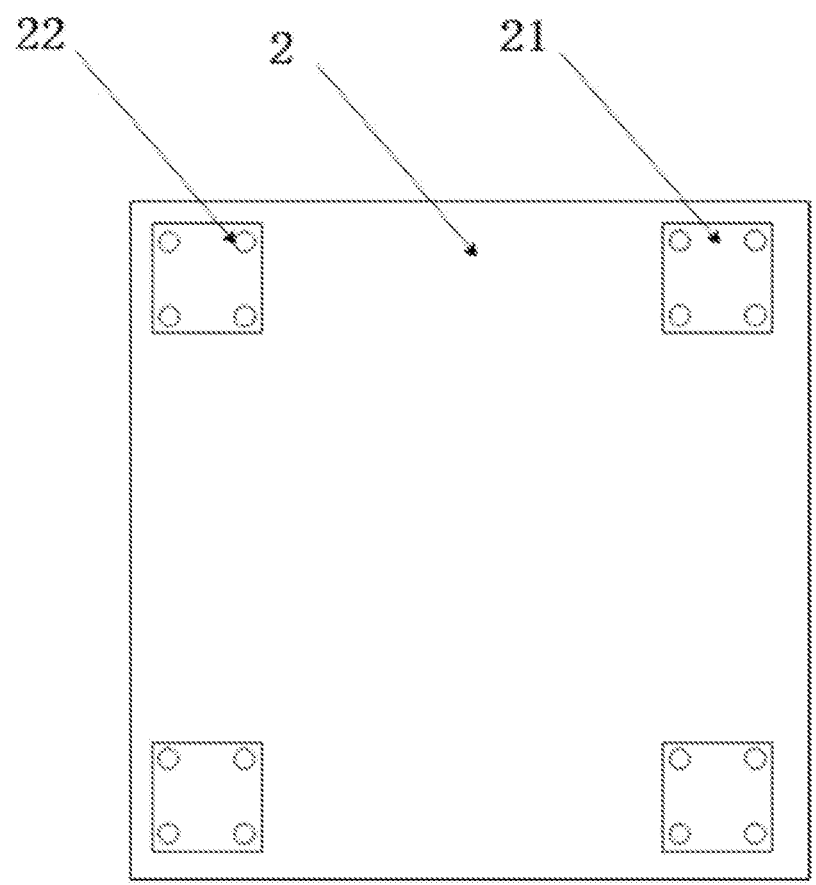
FIG. 7 is a structural schematic diagram of a sliding plate in an implementation method of the present disclosure.

In the embodiment, the transposition system may comprise twenty-four telescopic mechanical rods 5 and twenty-four sliding plates 2, and the twenty-four telescopic mechanical rods 5 and twenty-four sliding plates 2 are arranged in a one-to-one correspondence manner. The twenty-four sliding plates 2 are fixed on the rectangular test box and the upper cladding sheet through bolts 22, namely four telescopic mechanical rods 5 and four sliding plates 2 (as shown in FIG. 7) are installed on the upper cladding sheet, and four telescopic mechanical rods 5 and four sliding plates 2 are installed on each inner side face of the rectangular test box.

Further, as shown in FIG. 5, the telescopic mechanical rod 5 is arranged between the sliding plate 2 and the loading plate 4, one end of the telescopic mechanical rod 5 is slidably connected with the sliding plate 2, and the other end of the telescopic mechanical rod 5 is rotatably connected with the loading plate. Sliding assemblies (such as a sliding rail and a sliding block) are arranged on the sliding plate 2, and one end of the telescopic mechanical rod 5 is slidably connected with the sliding plate 2 through the sliding assemblies. The telescopic mechanical rod 5 can reach a telescopic effect through own characteristics, and two-dimensional plane sliding can be carried out on the surface of the sliding plate 2 through connecting parts among the sliding plates 2.

Or, the telescopic mechanical rod 5 is arranged between the sliding plate 2 and the loading plate 4, and anchoring connection is carried out through bolts 22 and anchoring parts 22.

Specifically, the control monitoring system comprises a control device 6 and monitoring devices, wherein the control device can be used for adjusting the telescopic mechanical rods 5 and the loading mechanical arms 3, and the monitoring devices can be used for monitoring strain data, related to anisotropy of an inclined consolidation material, of loading shear in the three-dimensional space. The control device 6 and the monitoring devices are respectively connected with a computer system.

Further, the monitoring devices comprise optical fiber sensors and/or a CCD camera; the optical fiber sensor is arranged on the inner side of the sliding plate 2, and is fixedly connected with the sliding plate 2 and the loading mechanical arm 3 through Z-shaped connecting parts; the CCD camera is arranged on the main body loading steel frame, and is fixedly connected with the main body loading steel frame; and the optical fiber sensors and the CCD camera are mutually independent monitoring devices.

During the loading process of the test, by using the optical fiber sensors on the inner sides of the sliding plates 2, the angles and the telescopic amounts of the six loading mechanical arms 3 are recorded, the continuous stain capacity and temperature variation condition of the soil body sample 7 are observed and recorded, the stress and relevant parameter results of loadings in all directions are calculated, and the stress path of the soil body sample 7 is calculated. Continuous and automatic photographing collection is carried out by using the CCD camera fixed on the main body loading frame 1, and the image data such as shear deformation form are observed. Corresponding recording frequency, such as 0.02 Hz, of the optical fiber sensors and the CCD camera can be selectively set according to requirements so as to adjust the collection interval. The optical fiber sensors and the CCD camera are mutually independent monitoring systems, and can be used singly or in a combined manner.

In the embodiment, the control device 6 is controlled by the computer system. The control device 6 can adjust the sliding directions, the sliding distances and the telescopic lengths of the twenty-four telescopic mechanical arms 5 through the computer system. Moreover, the control device 6 also can adjust the rotating angles, the telescopic angles and the loading force magnitudes of the six loading mechanical arms 3 through the computer system.

In the process that the control device 6 adjusts the rotating angle and the loading force magnitude of the six loading mechanical arms 3, the monitoring device can collect data such as the rotating angle, the telescopic length and the loading force magnitude, calculate the stress and the strain of the soil body sample 7 in the direction of the soil body sample 7 to form a time domain file, and export the file in a computer. Moreover, in the process that the control device 6 adjusts the sliding directions, the sliding distances and the telescopic lengths of the twenty-four telescopic mechanical rods, the monitoring device can also collect data such as sliding direction, sliding distance and telescopic length, and store the consolidation and deposition inclined state of the soil body sample 7 to calculate the stress and strain data, related to anisotropy of an inclined consolidation material, of loading shear in the three-dimensional space to form a calculation file, and export the file in the computer.

In the embodiment, a control method of the shear control instrument under a three-dimensional space condition comprises the following steps:

Step one,

Firstly preparing a cubic soil body sample, placing the cubic soil body sample on the loading plates with inner spherical grooves at the lower positions inside the main body loading steel frame, then covering up the detachable upper cladding sheet, then controlling the twenty-four telescopic mechanical arms by adjusting the control system, and adjusting the six loading plates with inner spherical grooves to be in complete contact with the soil body sample and to be fixed. After the cubic soil body sample is installed, different three-dimensional space angles can be adjusted according to the design requirements of the test, the solidification process of the cubic soil body sample with different deposition inclined surfaces is realized, and solidification loading in the main direction is realized through loading.

Step two,

After the cubic soil body sample is completely solidified, reducing the twenty-four telescopic mechanical rods, and adjusting the loading angles and the telescopic amounts of the six loading mechanical arms according to the design requirements of the test through the control device, and carrying out loading.

Wherein, the available loading modes comprise but not limited to the following loads.

Firstly, loading modes capable of realizing arbitrary rotation of main stress.

Secondly, loading modes capable of realizing arbitrary confining pressure in all main stress directions.

Thirdly, loading modes capable of realizing anisotropic shearing.

Fourthly, other all loading modes, none of the above conditions, which can be completed by the device.

Step three,

After the parameters, such as dimensions and weight, of the cubic soil body sample are input in the control monitoring system, clicking to start the test; in the loading process of the test, by using the optical fiber sensors on the inner sides of the sliding plates, recording the angles and the telescopic amounts of the six loading mechanical arms, observing and recording the continuous stain capacity and temperature variation condition of the soil body sample, calculating the stress and relevant parameter results of loadings in all directions and the stress path of the soil body sample 7, carrying out continuous and automatic photographing collection by using the CCD camera fixed on the main body loading frame, observing the image data such as shear deformation form. Recording frequency, such as 0.02 Hz, of the optical fiber sensors and the CCD camera can be selectively set according to requirements so as to adjust the collection interval of the optical fiber sensors and the CCD camera. The optical fiber sensors and the CCD camera are mutually independent monitoring systems, and can be used singly or in a combined manner.

Step four,

After test loading is finished, clicking to stop collection, and under the actions of the temperature and strain of the optical fiber sensors, generating an electrostrictive effect by the fiber cores of the optical fiber sensors to form text data according to measured data of the strain and temperature; meanwhile, carrying out continuous photographing by the CCD camera according to a certain time interval, collecting model images at a certain moment, and calculating the actual displacement of the grid center point of the cubic soil body sample by taking the image at the initial moment as a reference and according to the proportional relation of pixel displacement. According to the calculation mode of the actual displacement of the grid center point, calculating all the initial grid points to obtain a displacement field of the cubic soil body sample in the whole test area, and forming text data; and in combination with related samples and loading parameters input before the test, drawing a dynamic image in the test process of the cubic soil body sample, automatically selecting the coordinate axis of the image, and adjusting the dynamic image into a required graph so as to observe the test phenomenon of the cubic soil body sample.

In the embodiment, the soil body sample is loaded through the loading system, and the shear stress and normal stress coordinated change of the soil body sample is controlled under the coordinated adjustment of the transposition system and the control monitoring system, so that a fixed-axis shear stress path in which different stress principle axis directions are changed and the shear stress is gradually increased can be realized. A shear test with unchangeable deviatoric stress level and continuous change of a large principal stress direction angle is carried out, so that the problem that only three principal stress magnitudes and a single direction vector can be controlled in a soil mechanics test at the present stage can be solved, and simultaneous control for directions and size in the three-dimensional space is realized.

Exemplary Methods

Figure 8:
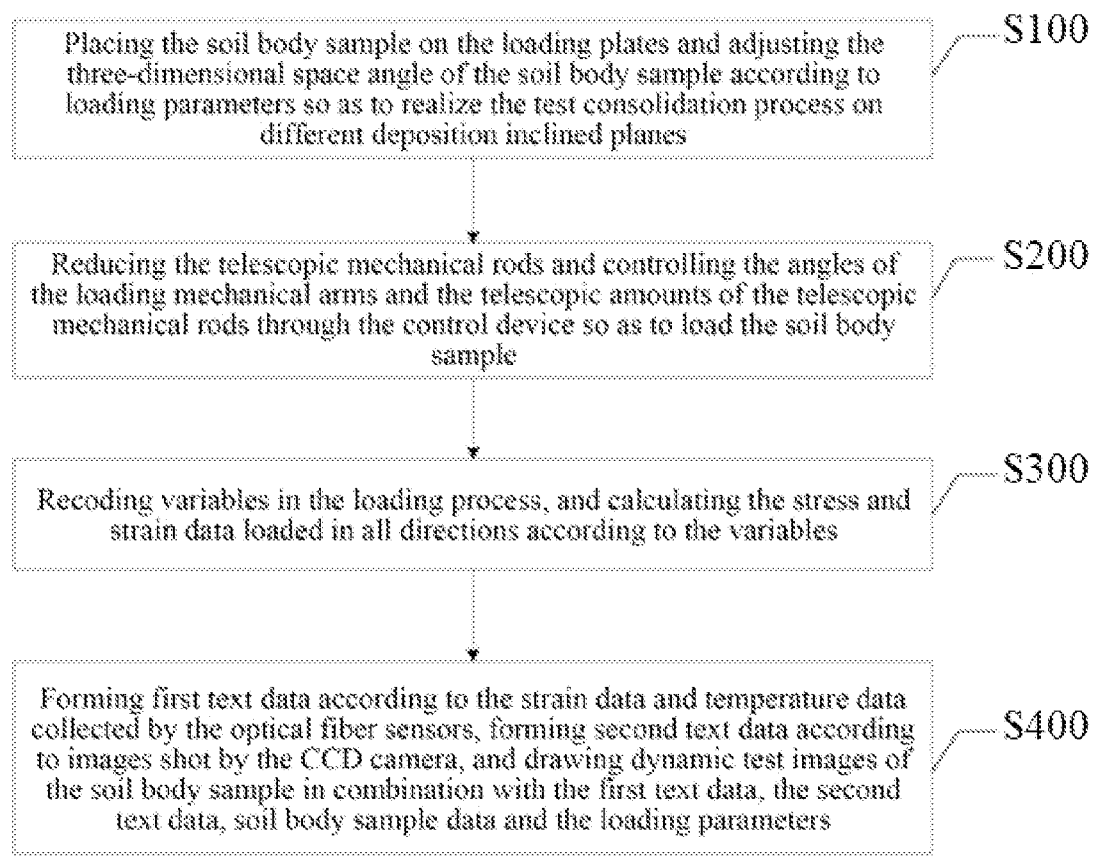
FIG. 8 is a flow diagram of a control method of a shear control instrument under a three-dimensional space condition in an implementation method of the present disclosure.

As shown in FIG. 8, the embodiment of the present disclosure provides a control method of a shear control instrument under a three-dimensional space condition, comprising the following steps:

Step S100, placing the soil body sample on the loading plates and adjusting the three-dimensional space angle of the soil body sample according to loading parameters so as to realize the test consolidation process on different deposition inclined planes.

In the embodiment, firstly preparing a cubic soil body sample (namely the soil body sample), when the cubic soil body sample is installed, firstly preparing a cubic soil body sample to be placed on the loading plates with inner spherical grooves at the lower positions inside the main body loading steel frame, then covering up the detachable upper cladding sheet, then controlling the twenty-four telescopic mechanical arms by adjusting the control system, and adjusting the six loading plates with inner spherical grooves to be in complete contact with the soil body sample and to be fixed. After the cubic soil body sample is installed, different three-dimensional space angles can be adjusted according to the design requirements of the test, the solidification process of the cubic soil body sample with different deposition inclined surfaces is realized, and solidification loading in the main direction is realized through loading.

Namely, in an implementation method, the step S100 specifically comprises the following steps:

Step S110, placing the soil body sample on the loading plates inside the main body loading steel frame;

Step S120, adjusting the control device, adjusting the telescopic mechanical rods, and adjusting the loading plates to be in complete contact with the soil body sample and to be fixed; and Step S130, obtaining the loading parameters, and adjusting the three-dimensional space angle of the soil body sample according to the loading parameters.

According to the embodiment, different three-dimensional space angles of the loading system are adjusted according to loading parameters, the consolidation process of soil body samples with different deposition inclined planes is achieved, and consolidation loading in the main direction is achieved through the mechanical arms.

As shown in FIG. 8, the embodiment of the present disclosure provides a control method of a shear control instrument under a three-dimensional space condition, comprising the following steps:

Step S200, reducing the telescopic mechanical rods and controlling the angles of the loading mechanical arms and the telescopic amounts of the telescopic mechanical rods through the control device so as to load the soil body sample.

In the embodiment, after the cubic soil body sample is completely solidified, reducing the twenty-four telescopic mechanical rods, and adjusting the loading angles and the telescopic amounts of the six loading mechanical arms according to the design requirements of the test through the control device, and carrying out loading.

Wherein, the available loading modes comprise but not limited to the following loads.

Firstly, loading modes capable of realizing arbitrary rotation of main stress.

Secondly, loading modes capable of realizing arbitrary confining pressure in all main stress directions.

Thirdly, loading modes capable of realizing anisotropic shearing.

Fourthly, other all loading modes, none of the above conditions, which can be completed by the device.

As shown in FIG. 8, the embodiment of the present disclosure provides a control method of a shear control instrument under a three-dimensional space condition, comprising the following steps:

Step S300, recoding variables in the loading process, and calculating the stress and strain data loaded in all directions according to the variables.

In the embodiment, the parameters, such as dimensions and weight, of the cubic soil body sample are input in the control monitoring system. In the loading process of the test, the angles and the telescopic amounts of the six loading mechanical arms are recorded, the stain capacity of the soil body sample is recorded, and the stress and relevant parameter results of loadings in all directions are calculated.

In the embodiment, the control device is controlled by the computer system. The control device can adjust the sliding directions, the sliding distances and the telescopic lengths of the twenty-four telescopic mechanical arms through the computer system. Moreover, the control device also can adjust the rotating angles, the telescopic angles and the loading force magnitudes of the six loading mechanical arms through the computer system.

Specifically, after the parameters, such as dimensions and weight, of the cubic soil body sample are input in the control monitoring system, clicking is carried out to start the test. In the loading process of the test, by using the optical fiber sensors on the inner sides of the sliding plates, the angles and the telescopic amounts of the six loading mechanical arms are recorded, the continuous stain capacity and temperature variation condition of the soil body sample are observed and recorded, the stress and relevant parameter results of loadings in all directions and the stress path of the soil body sample 7 are calculated, continuous and automatic photographing collection is carried out by using the CCD camera fixed on the main body loading frame, and the image data such as shear deformation form are observed. Recording frequency, such as 0.02 Hz, of the optical fiber sensors and the CCD camera can be selectively set according to requirements so as to adjust the collection interval of the optical fiber sensors and the CCD camera. The optical fiber sensors and the CCD camera are mutually independent monitoring systems, and can be used singly or in a combined manner.

Namely, in an implementation method, the step S300 specifically comprises the following steps:

Step S310, obtaining the dimension parameters and the weight parameter of the soil body sample;

Step S320, recording the angles of the loading mechanical arms, the telescopic amounts of the telescopic mechanical rods and the strain capacity of the soil body sample in the recording process; and Step S330, calculating the stress and strain data loaded in all directions, and forming calculation files according to the stress and strain data so as to export or display the calculation files.

According to the embodiment, stress and related parameter results loaded in all directions and the stress path of the cubic soil body sample can be calculated by using data collected by the optical fiber sensors on the inner sides of the sliding plates, continuous and automatic photographing collection is carried out by using the CCD camera fixed on the main body loading frame, and image data such as shear deformation form can be observed, so that a corresponding calculation file is formed, and reference is made for drawing of subsequent test dynamic images and test data analysis.

As shown in FIG. 8, the embodiment of the present disclosure provides a control method of a shear control instrument under a three-dimensional space condition, comprising the following steps:

Step S400, forming first text data according to the strain data and temperature data collected by the optical fiber sensors, forming second text data according to images shot by the CCD camera, and drawing dynamic test images of the soil body sample in combination with the first text data, the second text data, soil body sample data and the loading parameters.

Specifically, after test loading is finished, clicking is carried out to stop collection, and under the actions of the temperature and strain of the optical fiber sensors, an electrostrictive effect is generated by the fiber cores of the optical fiber sensors to form text data according to measured data of the strain and temperature; meanwhile, carrying out continuous photographing by the CCD camera according to a certain time interval, collecting model images at a certain moment, and calculating the actual displacement of the grid center point of the cubic soil body sample by taking the image at the initial moment as a reference and according to the proportional relation of pixel displacement. According to the calculation mode of the actual displacement of the grid center point, all the initial grid points are calculated to obtain a displacement field of the cubic soil body sample in the whole test area, and text data are formed; and in combination with related samples and loading parameters input before the test, a dynamic image is drawn in the test process of the cubic soil body sample, the coordinate axis of the image is automatically selected, and the dynamic image is adjusted into a required graph so as to observe the test phenomenon of the cubic soil body sample.

According to the embodiment, the soil body sample is loaded through the loading system, and the shear stress and normal stress coordinated change of the soil body sample is controlled under the coordinated adjustment of the transposition system and the control monitoring system, so that a fixed-axis shear stress path in which different stress principle axis directions are changed and the shear stress is gradually increased can be realized. A shear test with unchangeable deviatoric stress level and continuous change of a large principal stress direction angle is carried out.

Above all, the present disclosure provides a shear control instrument under a three-dimensional space condition and a control method of the shear control instrument. The shear control instrument under the three-dimensional space condition comprises a loading system, a transposition system and a control monitoring system, wherein the loading system is used for loading a soil body sample; the transposition system is connected with the loading system in an anchoring manner and is used for adjusting the direction of the loading system; and the control monitoring system is connected with the transposition system in an anchoring manner and is used for controlling the transposition system and monitoring test data. The soil body sample is loaded through the loading system, and the shear stress and normal stress coordinated change of the soil body sample is controlled under the coordinated adjustment of the transposition system and the control monitoring system, so that a fixed-axis shear stress path in which different stress principle axis directions are changed and the shear stress is gradually increased can be realized. A shear test with unchangeable deviatoric stress level and continuous change of a large principal stress direction angle is carried out, so that the problem that only three principal stress magnitudes and a single direction vector can be controlled in a soil mechanics test at the present stage can be solved.

It should be understood that the application of the present disclosure is not limited to the examples described above, and these modifications or variations can be made according to the above description for those skilled in the art, all of which are intended to fall within the scope of the appended claims.

What is claimed is:

1. A shear control instrument under a three-dimensional space condition, comprising a loading system, a transposition system and a control monitoring system, wherein the loading system is used for loading a soil body sample; the transposition system is connected with the loading system in an anchoring manner and is used for adjusting the direction of the loading system; and the control monitoring system is connected with the transposition system in an anchoring manner and is used for controlling the transposition system and monitoring test data;

the loading system comprises loading mechanical arms, loading plates and a main body loading steel frame;
one end of each of the loading mechanical arms is rotatably connected with the loading plate, and the other ends of the loading mechanical arms are rotatably connected with the control monitoring system; and the loading mechanical arms and the loading plates are fixedly connected with the main body loading steel frame through the transposition system;

the main body loading steel frame comprises a rectangular test box and an upper cladding sheet; and the rectangular test box is detachably connected with the upper cladding sheet;

the transposition system comprises telescopic mechanical rods for telescopically controlling the directions of the loading plates and sliding plates used for the telescopic mechanical rods to slide;

the sliding plate is fixedly connected with the rectangular test box through bolts; the sliding plate is fixedly connected with the upper cladding sheet through bolts; and the telescopic mechanical rod is slidably connected with the sliding plate;

sliding assemblies are arranged on the sliding plate, and one end of the telescopic mechanical rod is slidably connected with the sliding plate through the sliding assemblies.

2. The shear control instrument under a three-dimensional space condition according to claim 1, wherein an inner spherical groove is formed in one side of the loading plate, a spherical body is arranged at one end of the loading mechanical arm, and the dimensions of the inner spherical groove are matched with those of the spherical body; and the spherical body is embedded in the inner spherical groove, and the loading mechanical arm is rotatably connected with the loading plate through the spherical body.

3. The shear control instrument under a three-dimensional space condition according to claim 1, wherein the telescopic mechanical rod is arranged between the sliding plate and the loading plate, one end of the telescopic mechanical rod is slidably connected with the sliding plate, and the other end of the telescopic mechanical rod is rotatably connected with the loading plate.

4. The shear control instrument under a three-dimensional space condition according to claim 1, wherein the control monitoring system comprises a control device for adjusting the telescopic mechanical rods and the loading mechanical arms and monitoring devices for monitoring strain data, related to anisotropy of an inclined consolidation material, of loading shear in the three-dimensional space;

the control device and the monitoring devices are respectively connected with a computer system;

the monitoring devices comprise optical fiber sensors and/or a CCD camera; the optical fiber sensor is arranged on the inner side of the sliding plate, and is fixedly connected with the sliding plate; the CCD camera is arranged on the main body loading steel frame, and is fixedly connected with the main body loading steel frame; and the optical fiber sensors and the CCD camera are mutually independent monitoring devices.

5. A control method of a shear control instrument under a three-dimensional space condition, applied to the shear control instrument under a three-dimensional space condition according to claim 4, comprising the following steps:

placing the soil body sample on the loading plates and adjusting the three-dimensional space angle of the soil body sample according to loading parameters so as to realize the test consolidation process on different deposition inclined planes;

reducing the telescopic mechanical rods and controlling the angles of the loading mechanical arms and the telescopic amounts of the telescopic mechanical rods through the control device so as to load the soil body sample;

recoding variables in the loading process, and calculating the stress and strain data loaded in all directions according to the variables; and forming first text data according to the strain data and temperature data collected by the optical fiber sensors, forming second text data according to images shot by the CCD camera, and drawing dynamic test images of the soil body sample in combination with the first text data, the second text data, soil body sample data and the loading parameters.

6. The control method of a shear control instrument under a three-dimensional space condition according to claim 5, wherein the step of placing the soil body sample on the loading plates and adjusting the three-dimensional spatial angle of the soil body sample comprises the following substeps:

placing the soil body sample on the loading plates inside the main body loading steel frame;

adjusting the control device, adjusting the telescopic mechanical rods, and adjusting the loading plates to be in complete contact with the soil body sample and to be fixed; and obtaining the loading parameters, and adjusting the three-dimensional space angle of the soil body sample according to the loading parameters.

7. The control method of a shear control instrument under a three-dimensional space condition according to claim 5, wherein the step of recording variables in the loading process, and calculating the stress and strain data loaded in all directions according to the variables comprises the following substeps:

obtaining the dimension parameters and the weight parameter of the soil body sample;

recording the angles of the loading mechanical arms, the telescopic amounts of the telescopic mechanical rods and the strain capacity of the soil body sample in the recording process; and calculating the stress and strain data loaded in all directions, and forming calculation files according to the stress and strain data so as to export or display the calculation files.

\* \* \* \* \*